United States Patent [19]
Lee

[11] Patent Number: 5,917,884
[45] Date of Patent: Jun. 29, 1999

[54] TEMPLATE FOR ENSURING ACCURATE PATIENT POSITIONING FOR UPRIGHT X-RAY EXAMINATIONS

[76] Inventor: Aaron T. Lee, 25 Castle Dr., Stillwater, N.Y. 12170

[21] Appl. No.: 08/950,554

[22] Filed: Oct. 15, 1997

[51] Int. Cl.⁶ ........................................................ A61B 6/08
[52] U.S. Cl. ............................................. 378/205; 378/210
[58] Field of Search ............................................... 378/205

[56] References Cited

U.S. PATENT DOCUMENTS 3,700,894  10/1972  Counsell ................................. 378/205

Primary Examiner—Craig E. Church
Attorney, Agent, or Firm—James F. Cottone

[57] ABSTRACT

A template for aiding in the accurate alignment of a human subject undergoing upright X-ray examinations requiring one or more oblique views is formed of graphical indicia specially arranged for highly intuitive interpretation by the subject. The indicia include one or more lines of obliquity, as well as an orthogonal line, with which the subject aligns his feet responsive to instructions from an X-ray technician. In various preferred embodiments, a range of visual means is employed to ensure that stress-free and highly repeatable oblique views are obtained, these means including unique line patterns and orientations, as well as distinct line colors and shapes.

20 Claims, 1 Drawing Sheet

TEMPLATE FOR ENSURING ACCURATE PATIENT POSITIONING FOR UPRIGHT X-RAY EXAMINATIONS

TECHNICAL FIELD

The present invention relates generally to graphic indicia used for ensuring accurate patient alignment for X-ray examinations, and more particularly to a template-like system including predetermined lines of obliquity that are used by a patient and an X-ray technologist to accurately obtain the desired oblique radiographs called for by a clinician.

BACKGROUND

It has been conservatively estimated that for both routine and special radiographic studies requiring accurate subject positioning, an average of 3.5 positions per subject have been required in past years. Present diagnostic procedures not only often call for more views, but also require that previously produced views be repeated at some later time with a higher degree of accuracy. This necessity exists particularly in taking X-ray photographs with the patient upright (i.e., the vertical Bucky arrangement) when taking X-rays of the neck, dorsal, and lumbar spine, pelvis, and chest. Often, radiologic technologists have either had to rely on their judgement to position patients for upright exams —which involves the possibility of human error—or have had to employ large and clumsy patient alignment apparatus of all sorts, which frequently needlessly complicates the patient alignment process. Clearly, there are many benefits from accurate positioning of X-ray patients, some of the more obvious ones being: less repeats of X-rays due to inaccurate positioning; less radiation exposure to the patient and staff by reducing repeats; reducing facility costs of film and processing due to repeats; increased efficient use of staff due to more upright studies being easily achieved; plus others.

Because of the importance of producing the highest quality X-ray examinations and reducing the cost and patient exposure due to possible repeats, proper patient alignment has been the subject of much inventive effort over the years.

Descriptions of typical prior art approaches may be found in a number of U.S. patents. Illustrative early teachings of patient alignment aids are found in U.S. Pat. Nos. 2,552,592 to Rush and 3,524,057 to Hammonds. In the 1951 Rush patent there is described a patient-positioning device consisting of a base platform mounted on rollers or casters, which carries an additional pair of platforms—the first adjustable longitudinally, the second rotatable like a turntable—all to transport and align a patient standing on the top platform relative to a vertical Bucky diaphragm for X-ray exposure. The 1970 Hammonds patent also teaches the use of a platform mounted for rotation and lateral translation on which a patient stands adjacent a variably pivotable vertical X-ray film holder.

More recent teachings of basically the same approach, that of an X-ray patient standing on various types of platforms which are then rotated and/or translated, are found in U.S. Pat. Nos. 4,719,646 to Saunders et al. and 3,700,894 to Counsell. The 1972 Counsell patent describes apparatus wherein a patient is aligned relative to an X-ray film cassette via a rotatable stand on the apparatus, which further includes means for slipping a guide element over the patient's head. The 1998 Saunders et al. patent discloses a cart-like machine having a rotatable platform for supporting and aligning a patient, particular adapted for the preparation of X-ray photographs of the leg bone, and hip and knee joint structures. While each of these prior art approaches acknowledges the importance of accurate and repeatable alignment of patients relative to X-ray film holders, they apparently are addressing the alignment task with ever-increasing apparatus complexity, and basic cost effectiveness has clearly been sacrificed. It is this cost-effective need that the present invention admirably meets with its elegant and straightforward graphical indicia approach.

OBJECTS OF THE INVENTION

It is therefore a primary object of the present invention to provide improved methods and apparatus for optimally aligning a patient undergoing X-ray examinations, particular for those examinations that call for producing radiographs at one or more lines of obliquity.

A further object of the present invention is to provide a passive device that includes graphical indicia for aiding in the alignment and positioning of a patient undergoing upright X-ray exams.

A still further object of the present invention is to provide a passive device having graphical indicia in the form of lines of obliquity as part of a template that an X-ray subject may utilize in combination with easy-to-understand instructions from an X-ray technician.

A yet further object of the present invention is to provide a method for aiding in the accurate alignment of a patient undergoing upright X-ray exams by employing graphic indicia susceptible of highly intuitive interpretation by the patient upon receipt of simple prompts or instructions from an X-ray technician.

In various preferred embodiments, a flat template is formed in nominally semicircular shape from a plurality of lines terminating at a 180°+ arcuate boundary. A first pair of parallel diametrical lines serve to position the template in proper planar alignment with and distance from its associated X-ray film holder, while a plurality of radial lines—or lines of obliquity—clearly mark predetermined oblique angles with respect to the film plane. Upon the X-ray subject positioning himself or herself so as to straddle the desired line of obliquity with his feet, the required oblique view is ensured. Alternate embodiments describe a number of distinct template arrangements, and further describe the use of variously colored lines of different widths and shapes or continuities to increase the ease of understanding and use by the subject.

BRIEF DESCRIPTION OF THE DRAWINGS

Additional objects and advantages of the invention will become apparent to those skilled in the art as the description proceeds with reference to the accompanying drawings wherein.

BEST MODE FOR CARRYING OUT THE INVENTION

Figure 1:
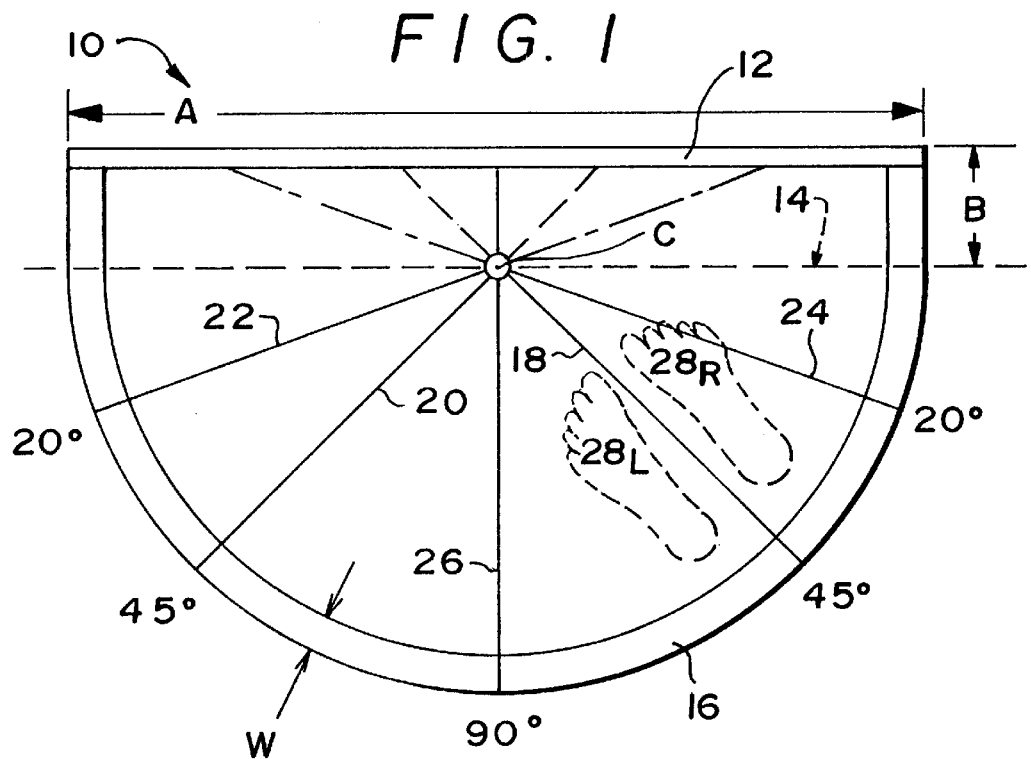
FIG. 1 is a plan view of an X-ray patient alignment template according to the present invention.
Figure 3A:
FIG. 3A–3C show various types of line patterns or shapes that may be employed to increase the X-ray patient's identification of particular lines of obliquity.
Figure 3B:
Figure 3C:
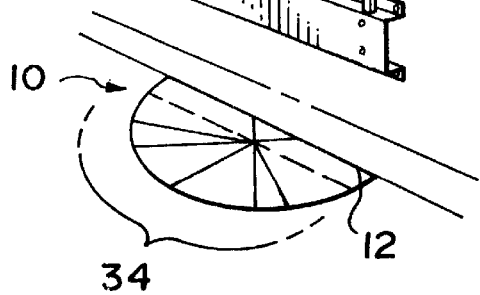

Referring now to FIG. 1 there is shown a plan view of a preferred X-ray alignment template according to the present invention. A flat template 10 is shown as it would appear upon being approached and viewed from above by a patient. By way of a brief overview, the template 10 is formed as a number of lines and arcs providing predetermined reference positions and directions, all of which are directed to aiding in the accurate positioning of a patient relative to a vertical film/camera plane by providing graphical alignment indicia on a floor for accurately positioning the patient's feet. An X-ray film holder (not shown) lies in a vertical plane parallel to and a short distance in front of a reference line 12 having length "A." An axis line 14 (shown in phantom) is positioned parallel to and a short distance "B" behind reference line 12. An axis point "C" located at the midpoint of axis line 14 serves as the point from which a plurality of radial lines, the lines of obliquity, emanate, all of which terminate on a template outer semicircular arc 16. A 'face left' 45° radial line of obliquity 18 is shown as extending from point C to arc 16, and may further extend (in dot/dashed lines) from point C to the reference line 12. Similarly, a 'face right' 45° radial line of obliquity 20, as well as 'face right' and 'face left' 20° radial lines 22 and 24, respectively, are shown. A 'face straight ahead' 90° radial line for full frontal patient view is shown as line 26. For increased subject intuitive understanding, the various lines are preferably identified in instructions by their graphical attributes rather than by their angular designations. As a further aid to discriminating the 'face left' lines from their 'face right' counter-parts, one of each pair may be formed as a continuous strip in a particular color while its counterpart may be formed in a contrasting shape, such as a wavy line or an intermittent (dashed) line, in the identical color. Momentary reference to the line shapes and patterns of FIGS. 3A–3C show some possibilities, FIG. 3A being a continuous line width, FIG. 3B being a dashed line, and FIG. 3C being a wavy line pattern.

In use, a patient positions his feet astraddle the appropriate template line of obliquity responsive to prompts or instructions from the X-ray technician to produce the selected X-ray view, as indicated by the dashed feet outlines 28R and 28L (not to scale) shown straddling the 'face left' 45° radial line 18. When a patient's feet are properly aligned with the various indicia, it is virtually assured that the remainder of his body will assume the desired oblique angle.

For improved patient and X-ray technician visibility, the several lines and arcs may be formed with appreciable thickness, and may be rendered in various colors and shapes. For the reference line 12 and the full 180°+ arc 16—the two outermost template indicia typical line widths may fall between 1 and 3 inches as denoted by a width symbol "W" on the arc 16. The width of radial lines 18, 20, 22, 24, and 26 may fall between ¾" and 1½", with the relative width of all lines and arcs adjusted for maximum visibility and clarity as perceived primarily by the patient. For simplicity of exposition, radial lines 18–26, and their dashed line extensions beyond point C, are shown as straight lines having no appreciable width. In a particularly preferred embodiment, the length of reference line 12 may fall between 20" and 30"; the two outer template indicia 12 and 16 may be rendered in bright yellow; the 20° radial lines may be rendered in red, the 45° radial lines may be rendered in blue, and the single 90° degree (orthogonal) line rendered in white. Judicious choice of the dimension B is made to accommodate typically encountered average patient sizes, and if a particular patient's size requires some deviation—especially in translation—as long as the patient's feet are parallel with and straddling the desired radial line, the correct and accurate degree of obliquity is ensured. Due to the various line widths that may be used, the point C is more properly depicted as a small circular region in lieu of a point.

Figure 2:
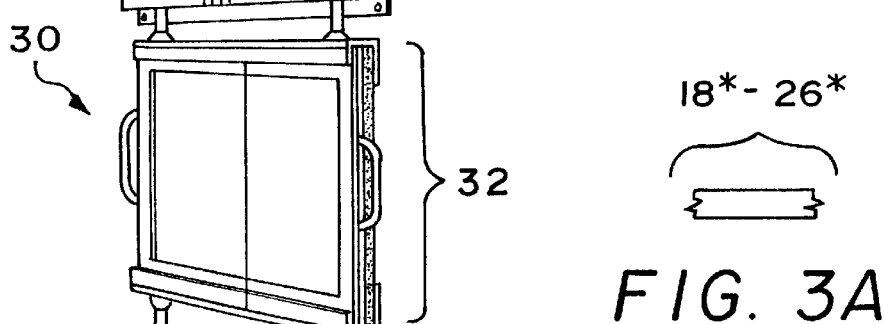
FIG. 2 is a perspective view of an X-ray patient alignment template suitably positioned in front of its associated upright X-ray film holder apparatus.

Operationally, the template 10 may be affixed to the floor in appropriate alignment with its associated upright X-ray film holder, as shown in FIG. 2. Therein, the template 10 has its reference line 12 positioned a predetermined distance from and parallel to the plane of the wall on which a Bucky Wall Stand 30 is mounted such that its vertically positionable film holder 32 and the template 10 produce the optimum subject views both in distance and in alignment. The various lines of obliquity are shown in FIG. 2 generally in the region 34. As previously indicated, use of the template 10 provides the ability to achieve the most accurate and repeatable radiographs for the upright examinations preferred by many physicians. However, it may also be used to produce accurately aligned examinations with a patient seated on a chair or stool. While any particular lines of obliquity may be employed, especially for highly specialized or experimental clinical needs, the 20° lines shown are considered useful for oblique examinations of the thoracic spine, etc.—while the 45° lines shown are considered useful for oblique examinations of cervical and lumbar spines, chest, ribs, and thorax.

When used in association with the fixed wall-mounted stand shown illustratively in FIG. 2, it is greatly preferred that the thin, flat template 10 be permanently affixed to the floor after initial alignment. For these uses, the template 10 is preferably prepared and applied in the form of a unitary preformed device and applied decal-like. Permanently tinted plastic and metallic foils are preferred for extended useful life of the various template line/arc portions, and commercially available heat, pressure, or time-setting adhesives may be employed to securely anchor the template to the floor or other horizontal surface. The template 10 may be formed as a continuous one-piece nominally semicircular sheet wherein the tinted lines and arcs are applied to a transparent substrate, the bottom surface of which carries a suitable adhesive layer. Alternately, the template 10 may be formed as a one-piece nominally semicircular, opened grid construct, with the various lines and arcs providing the interconnecting members that surround the intervening open areas.

Although the invention has been described in terms of selected preferred embodiment, the invention should not be deemed limited thereto, since other embodiments and modifications will readily occur to one skilled in the art. For example, the portions of the arc 16 between the reference line 12 and the axis line 14—as well as the dotted extension lines—may be deleted, producing a two-section template consisting of the reference line 12 and a semicircular portion having the outer arc and the various lines of obliquity. Additionally, each line of obliquity may be rendered in distinct colors and shapes (solid/dashed/wavy), and, of course, the lines/arc markings constituting the template may be applied on a floor stencil-like in lieu of the preferred decal-like approach described above. It is therefore to be understood that the appended claims are intended to cover all such modifications as fall within the true spirit and scope of the invention.

I claim:

1. A template for aiding in the accurate alignment of a subject with respect to an X-ray film plane for X-ray examinations requiring at least one oblique subject view, said template comprising:

(a) a reference line for establishing a template orientation parallel to said film plane;

(b) an arcuate line having extremities that terminate at said reference line, said two lines establishing outer template boundaries;

(c) a visible orthogonal line positioned within said template boundaries at right angles to said reference line and passing through a central axis area, said central axis area located adjacent the midpoint of said reference line;

(d) at least one visible line of obliquity positioned within said template boundaries at a predetermined angle with respect to said reference line and passing through said central axis area; and (e) whereby said visible orthogonal line aids in positioning the subject for an X-ray view not requiring an oblique view said at least one visible line of obliquity aids in positioning the subject for one or more X-ray views requiring an oblique view.

2. The template of claim 1 wherein said at least one visible line of obliquity is a first pair of lines of obliquity oriented at first acute angles with respect to said reference line and positioned on opposite sides of said visible orthogonal line.

3. The template of claim 2 further having a second pair of lines of obliquity oriented at second equal acute angles with respect to said reference line and positioned on opposite sides of said visible orthogonal line.

4. The template of claim 3 wherein said first equal acute angles are 20°.

5. The template of claim 4 wherein said second equal acute angles are 45°.

6. The template of claim 5 wherein said first and second pairs of visible lines of obliquity and said orthogonal line have line widths in the range of one-half inch to two inches.

7. The template of claim 6 wherein said first pair of visible lines of obliquity is rendered in a first color to aid the subject in identifying its associated line of obliquity.

8. The template of claim 7 wherein said second pair of visible lines of obliquity is rendered in a second color to aid the subject in identifying its associated lines of obliquity.

9. The template of claim 8 wherein said visible orthogonal line is rendered in a third color to aid the subject in readily identifying its associated line for assuming a position not requiring an oblique view.

10. The template of claim 9 wherein said two lines establishing template outer boundaries are visible and are formed in widths in the range of one inch to three inches and rendered in a color or shape or texture that visually distinguishes them from the various pairs of lines of obliquity and said orthogonal line.

11. The template of claim 7 wherein each member of said first pair of visible lines of obliquity is shaped so as to be visually distinct from the other pair member thereby further aiding the subject in identifying which one of the pair of lines of obliquity is desired for a particular oblique view.

12. The template of claim 8 wherein each member of said second pair of visible lines of obliquity is shaped so as to be visually distinct from the other pair member thereby further aiding the subject in identifying which one of the pair of lines of obliquity is to be used for a particular oblique view.

13. A template for aiding in the accurate alignment of a human subject with respect to an X-ray film plane for X-ray examinations requiring at least one oblique subject view guided by an operator's instructions, said template comprising:

(a) a reference line for establishing a template orientation parallel to said film plane and an arcuate line having its extremities terminating at said reference line, said two lines establishing the outer boundaries for said template;

(b) a visible orthogonal line having a width in the range of one-half inch to two inches positioned within said template boundaries at right angles to said reference line and located so as to pass through a central axis area, said central axis area located adjacent the midpoint of said reference line;

(c) at least one visible line of obliquity having a width in the range of one-half inch to two inches positioned within said template boundaries at a predetermined angle with respect to said reference line and passing through said central axis area; and (d) whereby said visible orthogonal line aids in positioning the subject for an X-ray view responsive to instructions not requiring an oblique view and said at least one visible line of obliquity aids in positioning the subject responsive to instructions for one or more X-ray views requiring an oblique view.

14. The template of claim 13 wherein said at least one visible line of obliquity is first and second pairs of lines wherein said first and second pairs are rendered in first and second distinct colors to aid the subject in identifying the desired line of obliquity by visually distinct means and said visible orthogonal line is rendered in a third color to aid the subject in readily identifying its associated line for assuming a position not requiring an oblique view.

15. The template of claim 14 wherein each member of said first and second pairs of lines of obliquity is shaped so as to be visually distinct from the other pair member thereby further aiding the subject in identifying which one of the pair of lines of obliquity and which orientation of that pair is desired for a particular oblique view.

16. A method of aiding in the accurate alignment of a human subject with respect to an X-ray film plane during upright X-ray examinations requiring one or more oblique subject views when guided by an operator's instructions, said method comprising the steps of:

(a) providing a template consisting of graphical indicia affixed to a floor in a predetermined position and orientation relative to a vertically disposed X-ray film holder apparatus;

(b) said graphical including an orthogonal line and at least one pair of lines of obliquity, each member of said at least one pair positioned at an acute angle from and on opposite sides of said orthogonal line; and (c) said orthogonal line providing visual guidance for aiding the subject in assuming a position not requiring an oblique view by positioning his feet astraddle said line responsive to instructions, and each member of said at least one pair providing visual guidance for aiding the subject in assuming a position for a desired oblique view by positioning his feet astraddle a particular member of said at least one pair responsive to instructions.

17. The method of claim 16 wherein said graphical indicia include a plurality of pairs of lines of obliquity, each pair positioned at distinct acute angles from said orthogonal line and each member of a pair disposed on opposite sides of said orthogonal line, whereby a plurality of desired oblique X-ray views may be facilitated by visually aiding the subject in identifying the desired line of obliquity and particular orientation responsive to instructions.

18. The method of claim 17 wherein said graphical indicia are formed as lines having widths in the range of one-half inch to two inches so as to be clearly visible to a subject standing over them.

19. The method of claim 18 wherein said orthogonal line is rendered in a color distinct from any other lines, and each of said plurality of pairs of lines of obliquity is rendered in a color distinct from all other pairs so as to aid the subject in identifying the various lines of obliquity by color rather than by its associated angular designation.

20. The method of claim 19 wherein each member of each pair of lines of obliquity is shaped so as to be visually distinct from the other pair member, thereby aiding the subject in identifying which one of the pair is desired for a particular oblique view and orientation.

* * * * *